(12) United States Patent
Zimmerman et al.

(10) Patent No.: US 8,032,372 B1
(45) Date of Patent: Oct. 4, 2011

(54) DICTATION SELECTION

(75) Inventors: Roger Scott Zimmerman, Wellesley, MA (US); George Zavaliagkos, Acton, MA (US)

(73) Assignee: eScription, Inc., Needham, MA (US)

( * ) Notice: Subject to any disclaimer, the term of this patent is extended or adjusted under 35 U.S.C. 154(b) by 698 days.

(21) Appl. No.: 11/225,794

(22) Filed: Sep. 13, 2005

(51) Int. Cl.
*G10L 15/26* (2006.01)

(52) U.S. Cl. ........ 704/235; 704/275; 704/270; 704/260; 704/257; 704/251; 704/232; 704/200; 704/2; 704/1; 705/34; 705/3; 382/310; 381/98

(58) Field of Classification Search ................ 704/235, 704/275, 232, 1, 256, 270, 260, 257, 251, 704/200, 2; 382/310; 705/34, 3; 381/98
See application file for complete search history.

(56) References Cited

U.S. PATENT DOCUMENTS

| | | | |
|---|---|---|---|
| 4,377,158 A | | 3/1983 | Friedman et al. |
| 5,033,088 A | | 7/1991 | Shipman |
| 5,036,539 A | | 7/1991 | Wrench, Jr. et al. |
| 5,146,439 A | | 9/1992 | Jachmann et al. ............. 369/25 |
| 5,179,627 A | | 1/1993 | Sweet et al. |
| 5,268,990 A | * | 12/1993 | Cohen et al. .................. 704/200 |
| 5,333,275 A | | 7/1994 | Wheatley et al. |
| 5,513,298 A | | 4/1996 | Stanford et al. |
| 5,519,808 A | | 5/1996 | Benton, Jr. et al. .......... 395/2.79 |
| 5,602,982 A | | 2/1997 | Judd et al. ..................... 395/326 |
| 5,615,296 A | | 3/1997 | Stanford et al. |
| 5,649,060 A | | 7/1997 | Ellozy et al. |
| 5,664,195 A | | 9/1997 | Chatterji |
| 5,727,950 A | | 3/1998 | Cook et al. |
| 5,748,888 A | | 5/1998 | Angelo et al. ................ 395/186 |
| 5,758,023 A | * | 5/1998 | Bordeaux ..................... 704/232 |
| 5,772,585 A | | 6/1998 | Lavin et al. |
| 5,787,230 A | | 7/1998 | Lee |
| 5,799,273 A | | 8/1998 | Mitchell et al. |
| 5,799,276 A | * | 8/1998 | Komissarchik et al. ...... 704/251 |
| 5,812,882 A | | 9/1998 | Raji et al. ..................... 395/892 |
| 5,819,220 A | | 10/1998 | Sarukkai et al. |
| 5,848,390 A | | 12/1998 | Matsumoto |

(Continued)

FOREIGN PATENT DOCUMENTS

JP 2000172483 6/2000

(Continued)

OTHER PUBLICATIONS

Batty et al., "The development of a portable real-time display of voice source characteristics", *IEEE*, 2:419-422 (2000).

(Continued)

*Primary Examiner* — Richemond Dorvil
*Assistant Examiner* — Michael Colucci
(74) *Attorney, Agent, or Firm* — Wolf, Greenfield & Sacks, P.C.

(57) ABSTRACT

A computer program product for computing a correction rate predictor for medical record dictations, the computer program product residing on a computer-readable medium includes computer-readable instructions for causing a computer to obtain a draft medical transcription of at least a portion of a dictation, the dictation being from medical personnel and concerning a patient, determine features of the dictation to produce a feature set comprising a combination of features of the dictation, the features being relevant to a quantity of transcription errors in the transcription, analyze the feature set to compute a predicted correction rate associated with the dictation and use the predicted correction rate to determine whether to provide at least a portion of the transcription to a transcriptionist.

24 Claims, 7 Drawing Sheets

U.S. PATENT DOCUMENTS

| | | | |
|---|---|---|---|
| 5,857,212 | A | 1/1999 | Van De Vanter ............... 707/519 |
| 5,875,448 | A | 2/1999 | Boys et al. ..................... 707/531 |
| 5,883,986 | A * | 3/1999 | Kopec et al. .................. 382/310 |
| 5,884,262 | A | 3/1999 | Wise et al. |
| 5,893,134 | A | 4/1999 | O'Donoghue et al. |
| 6,006,183 | A | 12/1999 | Lai et al. |
| 6,058,104 | A | 5/2000 | Snelling et al. |
| 6,058,426 | A | 5/2000 | Godwin et al. |
| 6,064,957 | A | 5/2000 | Brandow et al. |
| 6,076,059 | A | 6/2000 | Glickman et al. |
| 6,081,780 | A | 6/2000 | Lumelsky |
| 6,094,635 | A | 7/2000 | Scholz et al. |
| 6,101,467 | A | 8/2000 | Bartosik |
| 6,122,613 | A | 9/2000 | Baker |
| 6,122,614 | A | 9/2000 | Kahn et al. |
| 6,125,284 | A | 9/2000 | Moore et al. |
| 6,163,794 | A | 12/2000 | Lange et al. |
| 6,173,259 | B1 | 1/2001 | Bijl et al. |
| 6,192,339 | B1 | 2/2001 | Cox |
| 6,195,641 | B1 | 2/2001 | Loring et al. |
| 6,208,964 | B1 | 3/2001 | Sabourin |
| 6,260,011 | B1 | 7/2001 | Heckerman et al. |
| 6,263,308 | B1 | 7/2001 | Heckerman et al. |
| 6,269,188 | B1 | 7/2001 | Jamali |
| 6,282,652 | B1 | 8/2001 | Scheifler |
| 6,298,326 | B1 | 10/2001 | Feller |
| 6,308,158 | B1 | 10/2001 | Kuhnen et al. |
| 6,311,242 | B1 | 10/2001 | Falkenburg et al. |
| 6,327,568 | B1 | 12/2001 | Joost |
| 6,338,038 | B1 | 1/2002 | Hanson |
| 6,366,882 | B1 | 4/2002 | Bijl et al. |
| 6,374,225 | B1 | 4/2002 | Hejna, Jr. ...................... 704/270 |
| 6,415,256 | B1 | 7/2002 | Ditzik ............................ 704/231 |
| 6,434,526 | B1 | 8/2002 | Cilurzo et al. |
| 6,438,545 | B1 | 8/2002 | Beauregard et al. .............. 707/6 |
| 6,513,010 | B1 | 1/2003 | Lewin et al. |
| 6,526,380 | B1 | 2/2003 | Thelen et al. |
| 6,535,849 | B1 * | 3/2003 | Pakhomov et al. ........... 704/235 |
| 6,584,205 | B1 * | 6/2003 | Croft et al. ...................... 381/98 |
| 6,654,793 | B1 | 11/2003 | Wollrath et al. |
| 6,757,655 | B1 | 6/2004 | Besling et al. |
| 6,760,697 | B1 | 7/2004 | Neumeyer et al. |
| 6,766,294 | B2 | 7/2004 | MacGinite et al. |
| 6,785,654 | B2 | 8/2004 | Cyr et al. |
| 6,799,162 | B1 | 9/2004 | Goronzy et al. |
| 6,865,258 | B1 | 3/2005 | Polcyn ...................... 379/88.01 |
| 6,879,956 | B1 | 4/2005 | Honda et al. |
| 6,912,498 | B2 * | 6/2005 | Stevens et al. ................. 704/235 |
| 6,950,994 | B2 | 9/2005 | Dharap ......................... 715/864 |
| 6,961,699 | B1 | 11/2005 | Kahn et al. .................... 704/235 |
| 6,963,837 | B1 * | 11/2005 | Finke et al. .................... 704/256 |
| 6,996,445 | B1 | 2/2006 | Kamijo ........................... 700/94 |
| 7,006,967 | B1 | 2/2006 | Kahn et al. |
| 7,016,835 | B2 | 3/2006 | Eide et al. |
| 7,016,844 | B2 | 3/2006 | Othmer et al. ............. 704/270.1 |
| 7,031,918 | B2 | 4/2006 | Hwang |
| 7,236,932 | B1 | 6/2007 | Grajski ......................... 704/277 |
| 2001/0020226 | A1 | 9/2001 | Minamino et al. |
| 2001/0029452 | A1 | 10/2001 | Chen |
| 2002/0055845 | A1 | 5/2002 | Ueda et al. |
| 2002/0091527 | A1 | 7/2002 | Shiau |
| 2002/0138276 | A1 | 9/2002 | Damiba |
| 2002/0188452 | A1 * | 12/2002 | Howes .......................... 704/270 |
| 2002/0194000 | A1 | 12/2002 | Bennett et al. |
| 2003/0046080 | A1 | 3/2003 | Hejna, Jr. ...................... 704/270 |
| 2003/0046114 | A1 * | 3/2003 | Davies et al. ..................... 705/3 |
| 2003/0061135 | A1 * | 3/2003 | Waibel .......................... 705/34 |
| 2003/0067495 | A1 | 4/2003 | Pu et al. ........................ 345/811 |
| 2003/0083879 | A1 | 5/2003 | Cyr et al. |
| 2003/0083883 | A1 | 5/2003 | Cyr et al. |
| 2003/0154085 | A1 * | 8/2003 | Kelley .......................... 704/275 |
| 2004/0049385 | A1 * | 3/2004 | Lovance et al. .............. 704/235 |
| 2004/0064317 | A1 | 4/2004 | Othmer et al. |
| 2004/0088162 | A1 | 5/2004 | He et al. |
| 2005/0096910 | A1 * | 5/2005 | Watson et al. ................. 704/260 |
| 2005/0102140 | A1 * | 5/2005 | Davne et al. .................. 704/235 |
| 2005/0149747 | A1 | 7/2005 | Wesinger et al. ............. 713/200 |
| 2005/0165598 | A1 * | 7/2005 | Cote et al. ......................... 704/1 |
| 2006/0026003 | A1 * | 2/2006 | Carus et al. ................... 704/275 |
| 2006/0041428 | A1 * | 2/2006 | Fritsch et al. ................. 704/257 |
| 2006/0206943 | A1 | 9/2006 | Ellison et al. ................... 726/26 |
| 2006/0253895 | A1 | 11/2006 | Brandofino et al. .............. 726/2 |
| 2006/0272025 | A1 | 11/2006 | Mononen ........................ 726/26 |
| 2007/0143857 | A1 | 6/2007 | Ansari ............................ 726/26 |
| 2007/0276649 | A1 * | 11/2007 | Schubert .......................... 704/2 |
| 2007/0283444 | A1 | 12/2007 | Jang ................................ 726/26 |
| 2007/0294745 | A1 | 12/2007 | Tan et al. .......................... 726/2 |

FOREIGN PATENT DOCUMENTS

| | | |
|---|---|---|
| JP | 2002091477 | 3/2002 |
| WO | WO 00/31724 | 6/2000 |
| WO | WO 00/54252 | 9/2000 |
| WO | WO 02/075724 | 9/2002 |
| WO | WO 2004088635 | 10/2004 |

OTHER PUBLICATIONS

Cox, Stephen, "High-Level Approaches to Confidence Estimation in Speech Recognition," IEEE Transactions on Speech and Audio Processing, Oct. 2002, pp. 460-471, vol. 10, No. 7, IEEE, New York, NY.

Jiang, Hui, "Confidence Measures for Speech Recognition: A Study," Technical Report CS-2003-06, May 30, 2003, pp. 1-27, York University, Department of Computer Science, Ontario, Canada.

Kawahara, et al. "Dialogue Management Using Concept-Level Confidence Measures of Speech Recognition," date presently unknown, Kyoto University, School of Informatics, Kyoto, Japan and Ryukoku University, Otsu, Japan.

Litman, et al. "Automatic Detection of Poor Speech Recognition at the Dialogue Level," date presently unknown, AT&T Labs Research, Florham Park, NJ.

Mengusoglu et al. "Use of Acoustic Prior Information for Confidence Measure in ASR Applications," 2001, Faculte Polytechnique de Mons, TCTS Lab, Mons, Belgium.

Skantze, Gabriel, "The Use of Speech Recognition Confidence Scores in Dialogue Systems," Feb. 26, 2003, pp. 1-11, Department of Speech, Music and Hearing, KTH, Stockholm, Sweden.

Hazen, et al., "Recognition Confidence Scoring and Its Use in Speech Understanding Systems," Computer Speech and Language, 2002, pp. 49-67, vol. 16, Academic Press.

Gillick, et al., "A Probabilistic Approach to Confidence Estimation and Evaluation," Proceedings to IEEE Int'l Conf. on Acoustics, Speech, and Signal Processing, Apr. 1997, pp. 879-882.

Kemp et al, "Estimating Confidence Using Word Lattices," Proceedings to the 5th European Conf. on Speech Communication and Technology, Sep. 1997, pp. 827-830.

Maison, et al., "Robust Confidence Annotation and Rejection for Continuous Speech Recognition," Proceedings to IEEE Int'l Conf. on Acoustics, Speech, and Signal Processing, 2001.

Ma, et al., "A Support Vector Machines-Based Rejection Technique for Speech Recognition," Proceedings to IEEE Int'l Conf. on Acoustics, Speech, and Signal Processing, 2001.

Uhrik, C., "Confidence Metrics Based on N-Gram Language Model Backoff Behaviors," Proceedings to Eurospeech Conf., 1997.

Cox, et al., "A Semantically-Based Confidence Measure for Speech Recognition," Proceedings to the Int'l Conf. on Spoken Language Processing, 2000, Beijing, China.

Bohus et al., "Integrating Multiple Knowledge Sources for Utterance-Level Confidence Annotation in the CMU Communication Spoken Dialog System," Report CS190, 2002, Carnegie Mellon University.

Komatani, et al., "Flexible Mixed-Initiative Dialogue Management Using Concept-Level Confidence Measures of Speech Recognizer Output," Proceedings to the Int'l Conf. on Computational Linguistics (COLING), 2000.

San-Segundo, et al., "Confidence Measures for Spoken Dialogue Systems," Center for Spoken Language Research, University of Colorado, 2001.

Astley, et al., Customizeable Middleware for Modular Distributed Software, Communication of the ACM, May 2001, 1st paragraph p. 100, inset p. 101, last 1/2 of center column.

Clercq, "RPC Dynamic Port Allocation", Aug. 21, 2001, Available at www.winnetmag.com/Article/ArticleID/22206/22206.html.

Elmasri/Navathe, Fundamentals of Database Systems, pp. 76-79.

F. Jelinek, Self-Organized Language Modeling for Speech Recognition, pp. 450-505.

Hundt, et al., Speech Processing in Radiology, pp. 1451-1456.

Leggetter/Woodland, Maximum Likelihood Linear Regression for Speaker Adaptation of Continuous Density Hidden Markov Models, pp. 171-185.

Liskov, Primitive for Distributed Computing, CS Lab, MIT, ACM SIG on Operating Systems, pp. 38, section 3.3 2.sup.nd ; p. 35 2.sup.nd paragraph.

Neumeyer, et al., A Comparative Study of Speaker Adaptation Techniques, pp. 1127-1130.

Shinoda, et al., Unsupervised Adaptation Using Structural Bayes Approach, pp. 793-796.

Srinivasan "Binding Protocols for ONC RPC Version2", RFC 1833, Aug. 1995, Availabe at www.faqs.org/rfcs/frc_1833.html.

Srinivasan, "Remote Procedure Call Protocol Version 2"; RFC 1831, Aug. 1995, Available at www.faqs.org/rfcs/rfc1831.html.

Tanenbaum, A.S., "Distributed opearing systems anno 1992. What have we learned so far?", 1993, Distributed Systems Engineering 1, p. 3-10.

Zick, et al., Voice Recognition Software Versus a Traditional Transcription Service for Physician Charting in the ED, pp. 295-298.

Extended European Search Report for EP 05777492.9 dated Apr. 11, 2008.

Examination Report for GB 0703020 dated May 8, 2009.

International Search Report and Written Opinion for PCT/US05/26888 mailed Aug. 9, 2006.

* cited by examiner

Fraction of Samples with Actual Correction Rate Greater Than

| Predictor Value | 10% | 15% | 20% | 25% | 30% | 35% | Median Correction Rate |
|---|---|---|---|---|---|---|---|
| ≤ 12.3 | .5776 | .1877 | .0577 | .0180 | .0036 | .0000 | 10.9% |
| ≤ 13.5 | .6787 | .2906 | .0884 | .0216 | .0054 | .0000 | 12.1% |
| ≤ 14.5 | .7268 | .3417 | .1119 | .0300 | .0072 | .0000 | 12.7% |
| ≤ 15.5 | .7725 | .3925 | .1389 | .0415 | .0117 | .0000 | 13.5% |
| ≤ 16.7 | .8101 | .4555 | .1595 | .0498 | .0144 | .0014 | 14.4% |
| ≤ 18.0 | .8363 | .5012 | .1865 | .0589 | .0174 | .0012 | 15.0% |
| ≤ 19.5 | .8576 | .5492 | .2227 | .0789 | .0247 | .0030 | 15.7% |
| ≤ 21.0 | .8745 | .5898 | .2603 | .0943 | .0297 | .0040 | 16.2% |
| ≤ 23.0 | .8876 | .6301 | .3012 | .1207 | .0393 | .0072 | 16.8% |
| ≤ 34.5 | .8989 | .6649 | .3534 | .1660 | .0646 | .0158 | 17.3% |
| ≤ 36.2 | .8989 | .6652 | .3538 | .1666 | .0652 | .0158 | 17.5% |

FIG. 4

DICTATION SELECTION

BACKGROUND OF THE INVENTION

Healthcare costs in the United States account for a significant share of the GNP. The affordability of healthcare is of great concern to many Americans. Technological innovations offer an important leverage to reduce healthcare costs.

Many Healthcare institutions require doctors to keep accurate and detailed records concerning diagnosis and treatment of patients. Motivation for keeping such records include government regulations (such as Medicare and Medicaid regulations), desire for the best outcome for the patient, and mitigation of liability. The records include patient notes that reflect information that a doctor or other person adds to a patient record after a given diagnosis, patient interaction, lab test or the like.

Record keeping can be a time-consuming task, and the physician's time is valuable. The time required for a physician to hand-write or type patient notes can represent a significant expense. Verbal dictation of patient notes offers significant timesavings to physicians, and is becoming increasingly prevalent in modern healthcare organizations.

Over time, a significant industry has evolved around the transcription of medical dictation. Several companies produce special-purpose voice mailbox systems for storing medical dictation. These centralized systems hold voice mailboxes for a large number of physicians, each of whom can access a voice mailbox by dialing a phone number and putting in his or her identification code. These dictation voice mailbox systems are typically purchased or shared by healthcare institutions. Prices can be over $100,000 per voice mailbox system. Even at these prices, these centralized systems save healthcare institutions vast sums of money over the cost of maintaining records in a more distributed fashion.

Using today's voice mailbox medical dictation systems, when a doctor completes an interaction with a patient, the doctor calls a dictation voice mailbox, and dictates the records of the interaction with the patient. The voice mailbox is later accessed by a medical transcriptionist who listens to the audio and transcribes the audio into a text record. The playback of the audio data from the voice mailbox may be controlled by the transcriptionist through a set of foot pedals that mimic the action of the "forward", "play", and "rewind" buttons on a tape player. Should a transcriptionist hear an unfamiliar word, the standard practice is to stop the audio playback and look up the word in a printed dictionary.

Some medical transcriptionists may specialize in one area of medicine, or may deal primarily with a specific group of doctors. The level of familiarity with the doctors' voices and with the subject matter can increase the transcriptionist accuracy and efficiency over time.

The medical transcriptionist's time is less costly for the hospital than the doctor's time, and the medical transcriptionist is typically much more familiar with the computerized record-keeping systems than the doctor is, so this system offers a significant overall cost saving to the hospital.

To reduce costs further, health care organizations have deployed speech recognition technology, such as the AutoScript™ product (made by eScription™ of Needham, Mass.), to automatically transcribe medical dictations. Automatically transcribed medical records documents usually require editing by the transcriptionist.

In an application of background (as opposed to real-time) speech recognition to medical transcription, the automatic speech recognition process is run offline, i.e., without real-time clinician interaction. The speaker dictates and the speech recognition process is run in batch mode at another time. Draft transcriptions produced by the automatic speech recognition process may then be edited by the clinician or by a Medical Transcriptionist (MT) before being added to the medical record. An example of such an application is the EditScript™ product from eScription™.

Real-time and background speech recognition systems enroll and qualify clinicians using a prescribed quantity of training data, or in the case of most real-time ASR systems, by having the speaker dictate a specific text during an enrollment session. Once enrolled, all subsequent dictations for that speaker or speaker-worktype are processed through the speech recognition systems and transcriptions are created. For background ASR systems, these transcriptions are considered to be drafts manually edited by MTs before the final documents are uploaded into the electronic medical record. In real-time speech recognition applications, the words are transcribed as they are spoken, appearing on the computer screen for nearly immediate verification and editing by the clinician.

The yield of a background speech recognition application may be defined as the percentage of dictations which are able to be processed into draft transcriptions, as a fraction of the total number of dictations which enter the system. Generally, increasing the yield of an application reduces costs, so long as the drafts produced are of sufficient quality to save time when edited as compared to typing the transcription from scratch. Since draft transcriptions cannot be produced for a particular speaker until automatic speech recognition models exist for that speaker, there is an advantage in terms of system yield to create models with as little training as possible. However, drafts produced by ASR models based on very little training data generally lead to poorer quality draft transcriptions than would be possible by waiting for more training samples. Even with sufficient training data, some draft transcriptions require significant correction. For example, some drafts can produce more work for the MT than would typing the transcription from scratch, without the ASR device producing a draft. It may also be desirable to only allow editing of transcriptions that are substantially correct.

SUMMARY OF THE INVENTION

In general, in an aspect, the invention is directed to a computer program product for computing a correction rate predictor for medical record dictations. The computer program product resides on a computer-readable medium and comprises computer-readable instructions for causing a computer to obtain a draft medical transcription of at least a portion of a dictation, the dictation being from medical personnel and concerning a patient, determine features of the dictation to produce a feature set comprising a combination of features of the dictation, the features being relevant to a quantity of transcription errors in the transcription, analyze the feature set to compute a predicted correction rate associated with the dictation, and use the predicted correction rate to determine whether to provide at least a portion of the transcription to a transcriptionist.

Implementations of the invention may include one or more of the following features. The instructions can further cause a computer to compute an actual correction rate by comparing the draft medical transcription associated with the dictation and a corresponding edited transcription, and counting the number of corrections required to produce the edited transcription from the draft transcription, and compute a cumulative correction rate, or a correction rate prediction error, by comparing the predicted correction rate to the actual correction rate. The instructions can further cause a computer to modify the predictor to reduce the correction rate prediction error between the prediction and the actual correction rate. The instructions for causing a computer to obtain a draft medical transcription of a dictation can cause the computer to produce a draft transcription only if a prediction associated with the dictation is below a threshold probability. The computer program product can further cause the computer to compute the threshold by analyzing a behavior of the predictor on a subset of dictations that are stored in the database.

Further implementations of the invention may include one or more of the following features. The features include at least one of a background noise measure, overall audio quality measure, and a per-word confidence measure. The instructions for causing the computer to extract features can cause the computer to extract features for the entire transcription. The instructions for causing the computer to store the prediction can cause the computer to retrieve the predictor in accordance with one of a worktype, a speaker, a speaker-worktype pair, or a specialty associated with the transcription.

In general, in another aspect, the invention is directed to an automatic transcription processor module for processing a medical dictation transcription. The module is configured to obtain a dictation from a database, the dictation being stored in association with a correction rate predictor, compute a correction rate prediction for the dictation, the correction rate prediction indicating a quality of at least a portion of the dictation for production of a draft transcription, and produce a draft transcription for editing if the correction rate prediction for the dictation meets a criterion.

Implementations of the invention may include one or more of the following features. The language processor module can be configured to compare the correction rate prediction to a threshold value to determine whether to produce a draft transcription for the dictation. The language processor module can be further configured to produce a draft transcription for a portion of a dictation based on the correction rate prediction for a portion of the dictation. The language processor module can be configured to store the draft transcription and the correction rate prediction for the dictation in a database. The correction rate prediction stored in the database can be configured to determine whether a specific user utilizes the draft transcription. The module can be configured to compute a correction rate prediction for the dictation by combining features of the dictation, the features including one of a background noise measure, overall audio quality measure, and a per-word confidence measure.

Various aspects of the invention may provide one or more of the following capabilities. Time and cost of editing automatically generated medical transcription documents can be reduced. Transcriptionist editing time can be reduced. Transcriptionist fatigue in editing transcribed documents can be reduced. Stress associated with typing/editing, including physical stress, can be reduced. Drafts of medical transcription documents can be generated for speakers with lower training data requirements. Portions of dictations can be drafted, as opposed to all of a dictation or none of a dictation. Automatic adjustment for individual problems or differences (e.g., speaker has a cold or speaker enters an incorrect identification number) can be made. These and other capabilities of the invention, along with the invention itself, will be more fully understood after a review of the following figures, detailed description, and claims.

BRIEF DESCRIPTION OF THE FIGURES

FIG. 4 is an exemplary portion of a table for use in computing a threshold value associated with a correction rate predictor.

DETAILED DESCRIPTION OF PREFERRED EMBODIMENTS

Embodiments of the invention provide techniques for optimizing the throughput of a background speech recognition application. For example, selection of dictations can be moderated based on the acceptability of a draft transcription for editing. For example, an automatic speech recognition (ASR) system is supplemented by a correction rate predictor that is statistically trained and developed from a set of features extracted from a set of dictations. Whole dictation records or partial dictation records can be chosen for editing. Other embodiments are within the scope of the invention.

Figure 1:
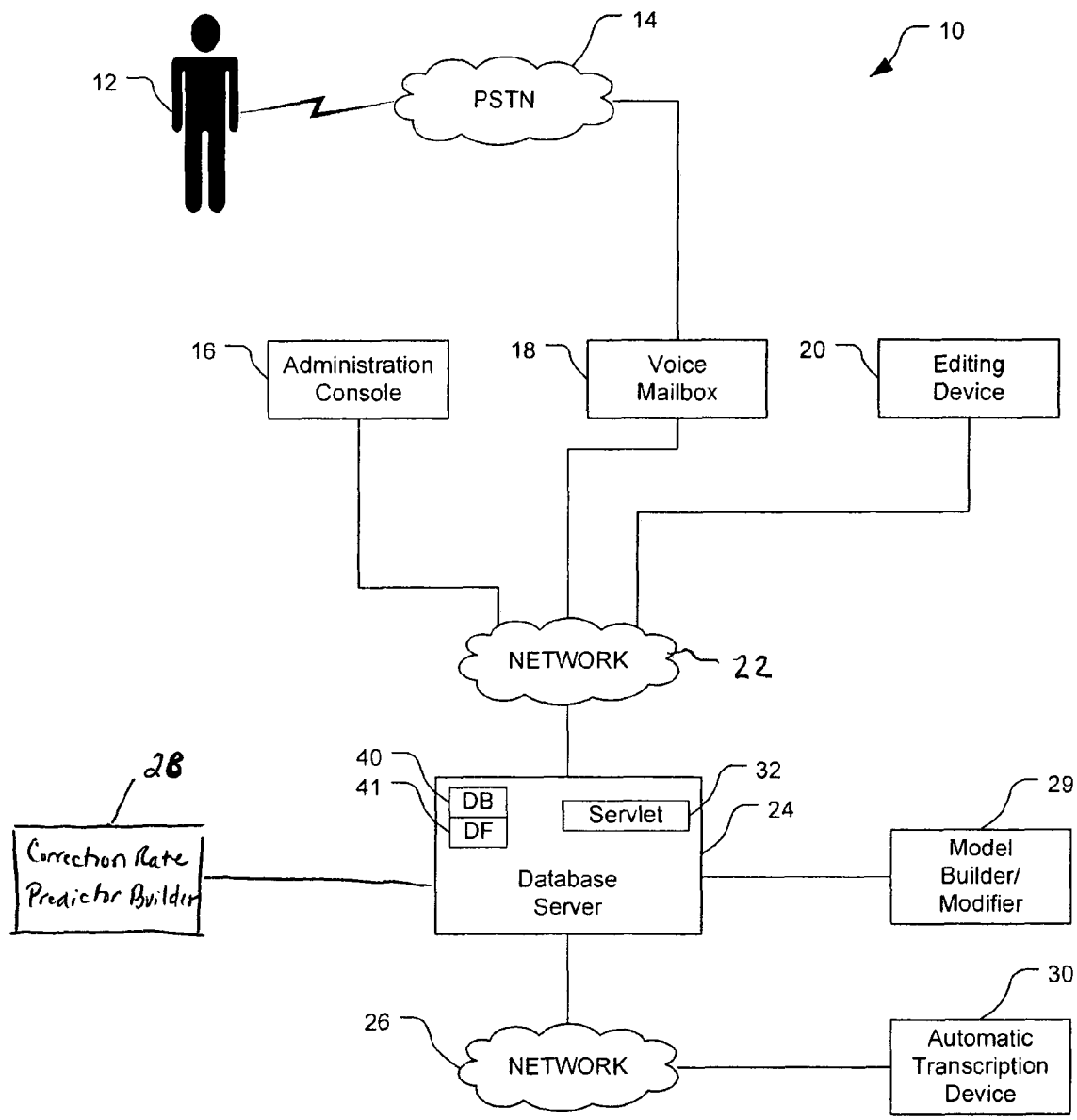
FIG. 1 is a simplified diagram of a system for transcribing dictations and editing corresponding transcriptions.

Referring to FIG. 1, a system 10 for transcribing audio and editing transcribed audio includes a speaker/person 12, a communications network 14, an administrative console 16, a voice mailbox system 18, an editing device 20, a communications network 22, a database server 24, a communications network 26, a correction rate predictor (CRP) builder 28, a model builder/modifier 29, and an automatic transcription device 30. Here, the network 14 is preferably a public switched telephone network (PSTN) although other networks, including packet-switched networks could be used, e.g., if the speaker 12 uses an Internet phone for dictation. The network 22 is preferably a packet-switched network such as the global packet-switched network known as the Internet. The network 26 is preferably a packet-switched, local area network (LAN). Other types of networks may be used, however, for the networks 14, 22, 26, or any or all of the networks 14, 22, 26 may be eliminated, e.g., if items shown in FIG. 1 are combined or eliminated. As discussed below, the model builder/modifier 29 is configured to build and/or modify automatic speech recognition (ASR) models (e.g., acoustic models, language models, formatting models) based on the training data for a speaker or speaker-worktype. Further, as discussed below, the CRP builder is configured to build a correction rate predictor from dictations.

Preferably, the voice mailbox system 18, the administrative console 16, and the editing device 20 are situated "off site" from the database server 24 and the automatic transcription device 30. These systems/devices 16, 18, 20, however, could be located "on site," and communications between them may take place, e.g., over a local area network. Similarly, it is possible to locate the automatic transcription device 30 off-site, and have the device 30 communicate with the database server 24 over the network 22.

The network 14 is configured to convey dictation from the speaker 12 to the voice mailbox system 18. Preferably, the speaker 12 dictates into an audio transducer such as a telephone, and the transduced audio is transmitted over the telephone network 14 into the voice mailbox system 18, such as the Intelliscript™ product made by eScription™ of Needham, Mass. The speaker 12 may, however, use means other than a standard telephone for creating the digital audio file for each dictation. For example, the speaker 12 may dictate into a handheld PDA device that includes its own digitization mechanism for storing the audio file. Or, the speaker 12 may use a standard "dictation station," such as those provided by many vendors. Still other devices may be used by the speaker 12 for dictating, and possibly digitizing the dictation, and sending it to the voice mailbox system 18.

The voice mailbox system 18 is configured to digitize audio from the speaker 12 to produce a digital audio file of the dictation. For example, the system 18 may use the Intelliscript™ product made by eScription.

The voice mailbox system 18 is further configured to prompt the speaker 12 to enter an identification code and a worktype code. The speaker 12 can enter the codes, e.g., by pressing buttons on a telephone to send DTMF tones, or by speaking the codes into the telephone. The system 18 may provide speech recognition to convert the spoken codes into a digital identification code and a digital worktype code. The mailbox system 18 is further configured to store the identifying code and the worktype code in association with the dictation. The identification code can associate the dictation with a particular speaker and/or an entity associated with the speaker (e.g., the speaker's employer or affiliate hospital, etc.). Speakers with multiple affiliations (e.g., to different entities such as hospitals) preferably have multiple identification codes, with each identification code corresponding to a respective one of the affiliated entities. The system 18 preferably prompts the speaker 12 to provide the worktype code at least for each dictation related to the medical field. The worktype code designates a category of work to which the dictation pertains, e.g., for medical applications this could include Office Note, Consultation, Operative Note, Discharge Summary, Radiology report, etc. The worktype code may be used to define settings such as database fields and/or to refine settings, such that settings may be specific not only to speaker-transcriptionist pairings, but further to worktype of dictations provided by the speaker, and/or to other parameters or indicia.

The voice mailbox system 18 is further configured to transmit the digital audio file and speaker identification code and worktype code over the network 22 to the database server 24 for storage. This transmission is accomplished by the system 18 product using standard network transmission protocols communicating with the database server 24.

The database server 24 is configured to store the incoming data from the voice mailbox system 18, as well as from other sources, in a database 40. The database server 24 may include the EditScript™ database product from eScription. Software of the database server is configured to produce a database record for the dictation, including a file pointer to the digital audio data, and a field containing the identification code for the speaker 12. If the audio and identifying data are stored on a PDA, the PDA may be connected to a computer running the HandiScript™ software product made by eScription that will perform the data transfer and communication with the database server 24 to enable a database record to be produced for the dictation.

The database 40 stores a variety of information regarding transcriptions. The database 40 stores the incoming data from the voice mailbox system 18, the database record produced by the database software, data fields associated with transcriptions, etc. The data fields are stored in a tabular data fields section 41, of the database 40, that includes sets of data fields associated with particular transcriptions. These fields may be accessed by the automatic transcription device 30, e.g., for storing data in the fields, or the administration console 18, e.g., for searching the fields for particular information.

Preferably, all communication with the database server 24 is intermediated by a "servlet" application 32 that includes an in-memory cached representation of recent database entries. The servlet 32 is configured to service requests from the voice mailbox system 18, the automatic transcription device, the editing device 20, and the administrative console 16, reading from the database 40 when the servlet's cache does not contain the required information. The servlet 32 includes a separate software module that helps ensure that the servlet's cache is synchronized with the contents of the database 40. This helps allow the database 40 to be off-loaded of much of the real-time data-communication and to grow to be much larger than otherwise possible. For simplicity, however, the below discussion does not refer to the servlet, but all database access activities may be realized using the servlet application 32 as an intermediary.

The automatic transcription device 30 may access the database in the database server 24 over the data network 26 for transcribing the stored dictation. The automatic transcription device 30 uses an automatic speech recognition (ASR) device (e.g., software) to produce a draft transcription for the dictation. An example of ASR technology is the AutoScript™ product made by eScription, that also uses the speaker identifying information to access speaker-dependent ASR models with which to perform the transcription. The device 30 transmits the draft transcription over the data network 26 to the database server 24 for storage in the database and to be accessed, along with the digital audio file, by the editing device 20 and by the CRP builder 28.

The CRP builder 28 may access the database 40 in the database server 24 to use data stored in the database to produce a correction rate predictor that can be used to predict the correction rate for a transcription. For example, the CRP builder 28 may access draft transcriptions and corresponding edited transcriptions for a speaker or speaker-worktype combination, along with associated ASR output data that are stored in the database 40. The CRP builder 28 builds a correction rate predictor to predict the actual correction rates for the set of transcriptions, using features derived from the ASR output data. The correction rate predictor stored in association with the speaker or speaker-worktype combination in the database 40.

The editing device 20 is configured to be used by a transcriptionist to access and edit the draft transcription stored in the database of the database server 24. The editing device 20 includes a computer (e.g., display, keyboard, mouse, monitor, memory, and a processor, etc.), an attached foot-pedal, and appropriate software such as the EditScript Client™ software product made by eScription. The transcriptionist can request a dictation job by, e.g., clicking an on-screen icon. The request is serviced by the database server 24, which finds the dictation for the transcriptionist, and transmits the corresponding audio file and the draft transcription text file, as stored in the database. The database server 24 locates dictations according to a CR-prediction, which is stored with the dictation, such that transcriptions are delivered to transcriptionists according to defined CR-prediction thresholds, as described below.

The transcriptionist edits the draft using the editing device 20 and sends the edited transcript back to the database server 24. For example, to end the editing session the transcriptionist can click an on-screen icon button to instruct the editing device 20 to send the final edited document to the database server 24 via the network 22, along with a unique identifier for the transcriptionist.

With the data sent from the editing device 20, the database in the server 24 contains, for each dictation: a speaker identifier, a transcriptionist identifier, the digital audio signal, and the edited text document.

The edited text document can be transmitted directly to a customer's medical record system or accessed over the data network 22 from the database by the administrative console 16. The console 16 may include an administrative console software product such as Emon™ made by eScription.

The raw and edited versions of a transcription, along with the audio for the dictation, may be used by the model builder/modifier 29 to produce acoustic, language and formatting models for the speaker or speaker-worktype. The audio files and raw and edited versions of transcriptions associated with their respective speaker and worktype identifiers are stored in the database 40. The model builder/modifier 29 uses the audio and transcriptions for each speaker to build or modify models for the speaker (and/or speaker and worktype) based on training data for a speaker. These models are stored in the database 40 so that they may be accessed and used by the automatic transcription device 30 to create a draft transcription for a subsequent dictation.

Figure 2:
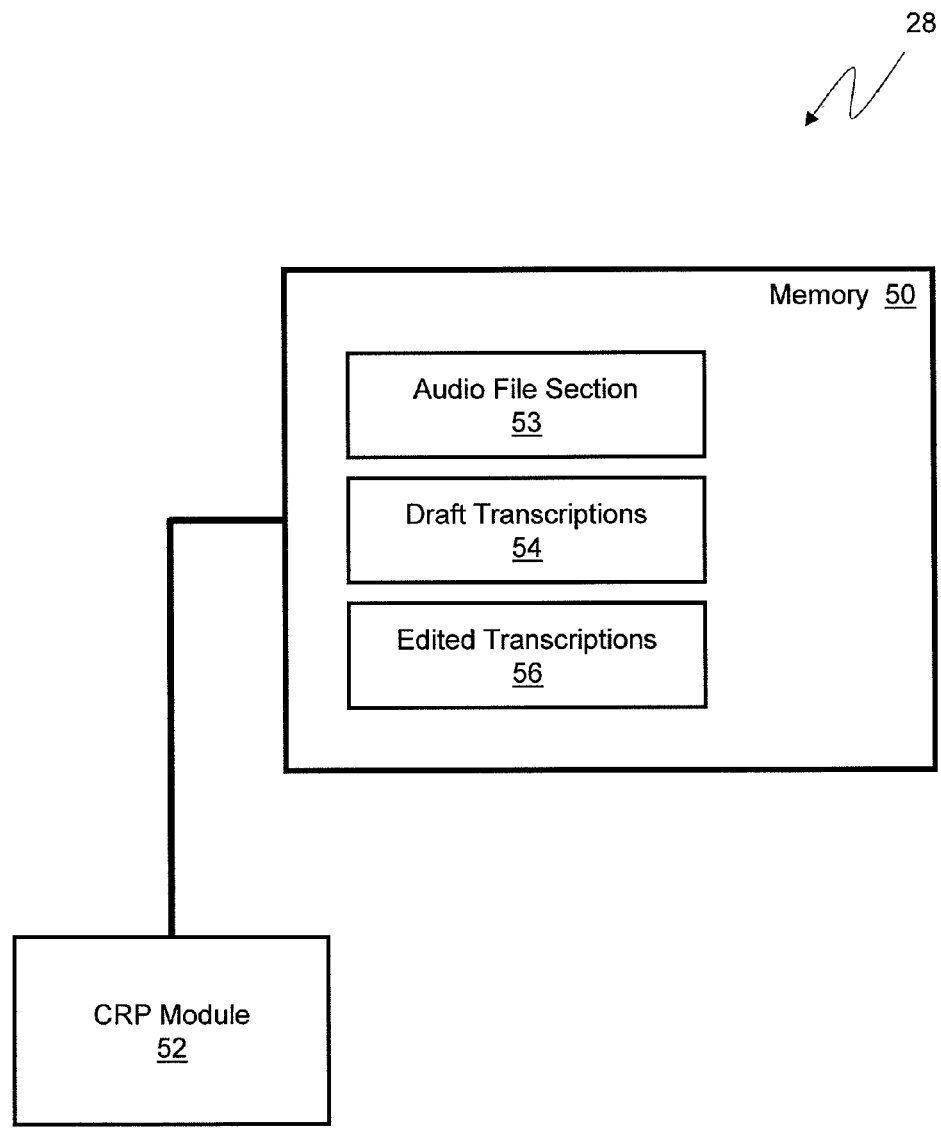
FIG. 2 is a block diagram of components of a correction rate predictor builder shown in FIG. 1.

Referring to FIG. 2, the CRP builder 28 includes a memory 50 and a CRP module (e.g., software) 52. The CRP module 52 includes memory and a processor for reading software code stored in the memory 50 and for executing instructions associated with this code for performing functions described below. The memory 50 includes an audio file section 53, a draft transcriptions section 54 and an edited transcriptions section 56. The audio file section 53 includes audio files for dictations recorded via the system 10. The draft transcriptions section 54 includes draft transcriptions that have not been edited by a transcriptionist. The edited transcriptions section 56 includes edited transcriptions associated with a draft transcription that have been edited by a particular transcriptionist and stored in the database 24. The CRP module 52 is configured to compute features for each audio file that are used to compute a correction rate prediction. The process of deriving the features from the audio file is described below (see FIG. 3 and associated description). The prediction is compared to the actual correction rate, which is computed by comparing the draft transcription with the edited transcription, each of which is associated with the audio file. A correction rate predictor results. The predictor substantially reduces (possibly minimizes) the difference between the CR prediction and the actual CR across the set of data. The parameters of the predictor are modified during the predictor building process to achieve this reduction. The prediction parameters include a prediction threshold that can be selected to optimize the tradeoff between yield and correction rate for the data set. The predictor is stored in the database 24 in association with at least one of the entire data set, or the data subset corresponding to a worktype, a speaker, a speaker/worktype pair, or a specialty, for example.

Figure 3:
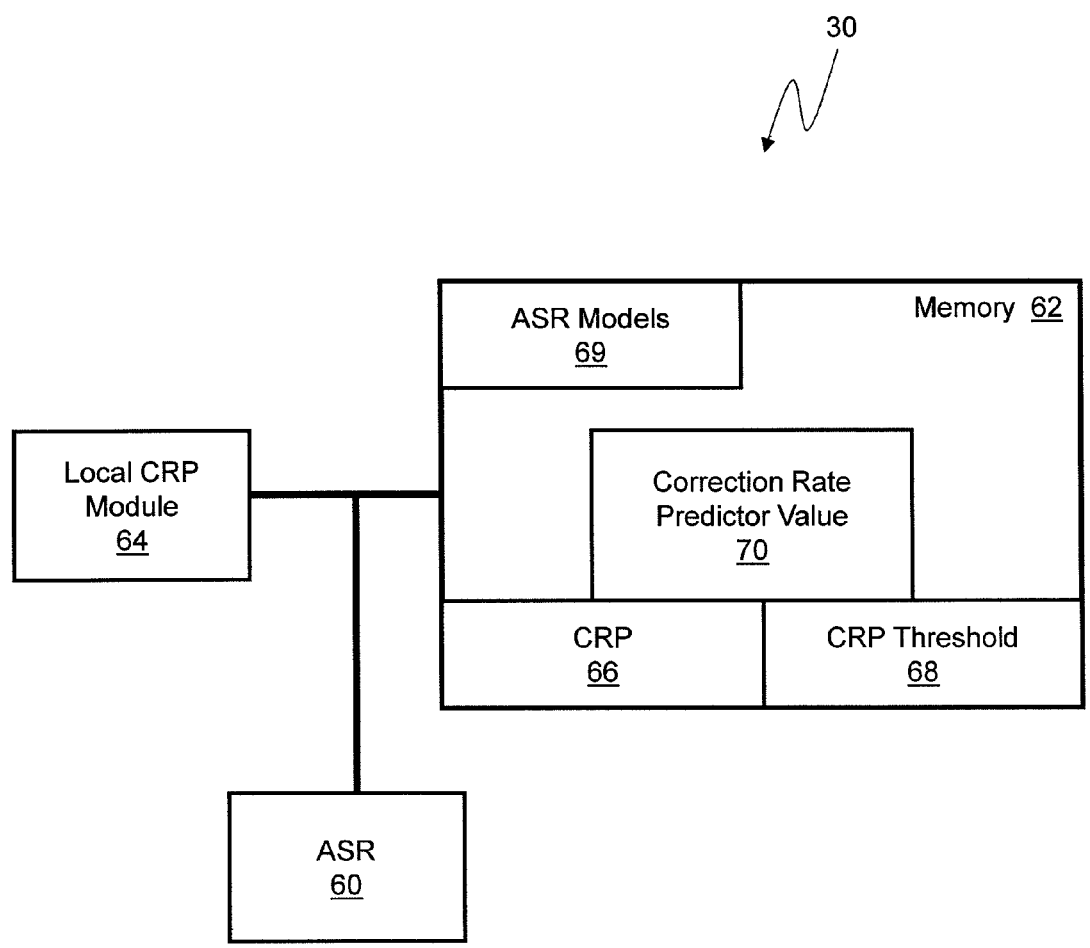
FIG. 3 is a block diagram of components of an automatic transcription device shown in FIG. 1.

Referring also to FIG. 3, the automatic transcription device 30 includes an ASR module 60, a memory 62 and a local CRP module 64. The local CRP module 64 is configured to compute feature values and the CR-prediction based on these values, similar to the function of the CRP module 52 in the CRP builder 28. The features include characteristics of the dictation that are evaluated to determine the quality of a dictation for production of a draft transcription. The ASR module 60 uses the ASR models 69, stored in the memory 62 to compute a transcribed text, along with associated ASR output data such as word lattices, word alignments and energy values from the digital audio file. This process is also used in the CRP module 52 as input to the production of the feature values for each dictation used in building the predictor. The local CRP module 64 is configured to analyze the output data from the ASR module 60, and to compute the feature values and the correction rate prediction from the feature values. The memory 62 includes a local copy of a correction rate predictor (CRP) 66, and a correction rate prediction value 70. The CRP 66 is the result of the CRP builder process and is accessed from the database 24. The local CRP module 64 is configured to access/use the CRP 66 to compute the CRP value 70 (i.e., the CRP module 64 is configured to compute a metric to indicate what quality of a draft will result from a dictation).

Referring to FIGS. 1-3, the local CRP module 64 and CRP builder 28 are both configured to compute features for each dictation. The CRP builder 28 is configured to build a correction rate predictor. The local CRP module 64 is configured to compute the CRP value 70. Thus, the local CRP module 64 and the CRP builder 28 compute substantially the same set of features in order to calculate the predicted correction rate for a dictation. Features are extracted from the ASR output data for a dictation while the dictation is being recognized. Features include measures of background noise, measures of overall audio quality such as noise/signal ratio or average spectrum, standard measures of per-word confidence (e.g., the percentage of word-lattice paths that contain a word over a given period of the audio), per-word confidence measures combined across all of or a portion of a dictation, and scores from models used in a speech recognition process (e.g., an acoustic-model score, a language-model score, a model of allowable/typical word durations, etc.). Features can be made specific to certain words in the raw word recognition output. For example, an average of the per-word confidence feature for all content words (i.e., all words excluding articles, prepositions, conjunctions, etc.) can be computed over non-silence sections of a dictation.

The local CRP module 64 and the CRP builder 28 combine features associated with each dictation. For example, the features can be combined according to an artificial neural network (ANN) into a classifier that is configured to predict the correction rate for a selected dictation. The classifier is configured to estimate the amount of work required to edit a draft transcription into a final version of the transcription. The classifier is trained, preferably offline, to predict the correction rate for a dictation. For example, the classifier is trained by collecting features for many dictations in the system. The classifier is built by iteratively modifying the parameters of the ANN such that the output of the new classifier is, on average, closer than a first classifier value to the actual correction rate across the data set used in building the predictor. Correction rates can be computed by comparing a draft transcription with its edited version, and counting the number of corrections needed to produce a final transcription from the draft, as is conducted in the CRP builder 28. The number of corrections can be in terms of, for example, space-separated tokens, characters, keystrokes, etc. For example, the draft transcription word sequence and the edited transcription word sequence can be compared using a Levenshtein distance. Alternatively, a weighted Levenshtein distance can be used to model the cost of particular word substitutions, deletions, or insertions according to the amount of time it takes to make such an edit.

The database 40 contains the history of text documents produced from the speaker's dictations, as well as the automatic transcriptions of the speaker's dictations provided by the automatic transcription device 30. The features are derived by re-computing the output data of the automatic transcription device 30 in a process in the CRP builder 28, preferably offline, or by storing this data at the time the dictation is being recognized by uploading it from the automatic transcription device 30 to the database 40. The correction rate predictor computed by the CRP builder 28 and used by the CRP module 64 is updated, e.g., periodically, as more dictations are gathered for the speaker over time. In this way, the models can track changes in the speaker's speaking style. The CRP module 64 preferably uses the updated model for the next transcription to be analyzed from the particular speaker. Further, the CRP builder 28 may weight more recent transcriptions from the speaker more heavily than earlier transcriptions to help account for changes in the speaker's style.

The CRP builder 28 can be configured to construct models that are speaker-dependent, speaker-worktype dependent, etc., such that threshold values can be conditioned on particular variables. Referring to FIG. 4, the threshold value is computed by analyzing the behavior of the CR-predictor on a subset of dictations from the database. A table of actual correction rates 80 includes a predictor value 82, actual correction rate percentages 84 and a median correction rate value 86. Each row illustrates the distribution of actual correction rate values on a set of data, given a predictor value which is less than or equal to a given threshold. Each row represents an increment of 10% of a total body of the test dictations (i.e., 100% of the test data had a CR predictor value less than or equal to 36.2). For example, for a predictor value 82 less than or equal to 18.0, 83.63% of the test data had an actual correction rate of greater than 10%, 50.12% of the data has an actual correction rate of greater than 15%, etc. The median correction rate value 86 represents the median value for the data in a row.

The threshold values for the correction rate predictor can be determined to effect a desired tradeoff between the percentage of dictations to be edited (as opposed to typed) and the median correction rate of those dictations. For example, in FIG. 4, setting a threshold value of 18.0 moves the median correction rate of the recognized dictations from 17.5% to 15.0%. Alternatively, the threshold can be set such that no more than a desired percentage of the to-be-edited dictations have correction rate values above a value that is deemed unacceptable. For example, if it is determined that no more than 5% of the edited data should have a CR value above 30, the CR predictor threshold can be set at 23.0, since 3.93% of the data that passes that threshold exceeds the CR value of 30. Setting the CR-predictor threshold to 23.0 results in approximately 20% of the data being typed, as opposed to edited.

If the correction rate prediction value computed by the local CRP module 64 is less than or equal to the threshold value computed at the CRP builder 28, the dictation is deemed qualitatively appropriate for automated production of a draft for editing. If the correction rate prediction value is more than the threshold value, the dictation is not of quality for automated production of a draft transcription.

At speech-recognition time, the automatic transcription device 30 downloads the audio, speakerID, WorkTypeID, and CR predictor associated with each given dictation. The CR predictor is accessed from the database 24 using the speakerID and workTypeID associated with the dictation. The CR predictor is derived from the parameters of the predictor function itself (e.g. the weights of the artificial neural network), and the threshold value to determine subsequent workflow.

The ASR module 60 completes varying amounts of computation in order to compute the output data needed to calculate the CRP features. For example, if the CR predictor uses only background noise level and average audio spectrum as features, the feature values may be computed using substantially simple signal processing techniques. Other feature sets may require more computation. For example, computing per-word confidence features may require that a word-lattice be created such that the percentage of lattice paths traversing each word can be computed. Features can be designed to be computed without actually constructing the draft transcription. Feature sets may not require formatting steps on the raw word output of the ASR module 60.

The CRP threshold is adapted based on speaker-dependent or speaker-worktype dependent data. The CRP threshold begins as a speaker-independent threshold, and is altered based on observation of the behavior of speaker-specific dictations. If the dictations that are below the threshold have lower actual correction rates than the speaker-independent thresholds, the CRP builder 28 increases the CR-prediction threshold for the speaker and stores the updated value in their CR-predictor in the database. If the actual correction rates are higher, the threshold for the speaker is decreased.

Drafts associated with dictations that are not initially edited, e.g., dictations with correction values above the threshold value, can be saved and used in determining a CR value for a speaker. Medical transcriptionists can transcribe the dictation from scratch, as in the normal workflow. A "pseudo CR" can be associated with the dictation by assuming that the final document produced by typing was actually produced by editing the draft. Once statistically significant dictations have gone through the system for a speaker, the feature set and predictor parameters may be adapted from the speaker-independent CR predictor by using the speaker's dictations in the CR predictor builder 28, for example, using a classification framework such as ANN training.

The CR predictor allows the automatic transcription device 30 to create drafts for some dictations based on less well-trained ASR models, e.g., for speakers with fewer dictations in the system. The yield of the system 10 may be increased by lowering the training data requirements for speakers. A model deployed based on small amounts of training data may include the CR predictor as a filter on which drafts are produced by the automatic transcription device 30. Once the ASR models for that speaker can be updated with more training data (collected in the database as part of the system operation), it may be possible to remove the filter and produce drafts for substantially all of a speaker's dictations. Generally, a CR predictor can be effective for a speaker having little data, i.e., a speaker's CR predictor need not be initialized by that speaker's data.

The local CRP module 64 is further configured to define segments within dictations on which to apply the CR predictor. These segments may be identified as sufficiently long intervals of relatively high acoustic energy between regions of relatively low acoustic energy, or based on certain semantically-meaningful "trigger" words or phrases found during the ASR decoding process. For example, many medical dictations of office visits are divided verbally by the clinician into "Subjective", "Objective", "Assessment", and "Plan" sections. The words (or semantically identical triggers such as "Reason for Visit", "Physical Examination", "Impression", "Recommendations") can be used by the local CRP module 64 to demarcate separate sections of the dictation. The sections may be treated by the CR predictor as dictations unto themselves. The automatic transcription device 30 can produce draft transcriptions for the sub-sections of the dictation which satisfy the CR predictor thresholds. The MT may receive at the editing device a draft transcription that requires some typing and some editing.

The database 24 stores a CRP threshold for each medical transcriptionist (MT) in the database 40. The threshold value associated with a MT is used to determine if any given editing job will be allocated to that MT. For example, if a dictation which has been recognized has an associated CR-prediction value, along with its draft transcription, the system 10 can be configured to only allocate that editing job to MTs whose CR-prediction threshold is less than or equal to that value (or null, for MTs that can edit any draft). An MT's CR-predictor threshold can be altered at the administrative console 18. Alternatively, an MT's CR-predictor threshold can be set automatically. For example, as shown in FIG. 4, a data set can be selected for a given transcriptionist, instead of evaluating the table for a speaker or a speaker-worktype.

Figure 5:
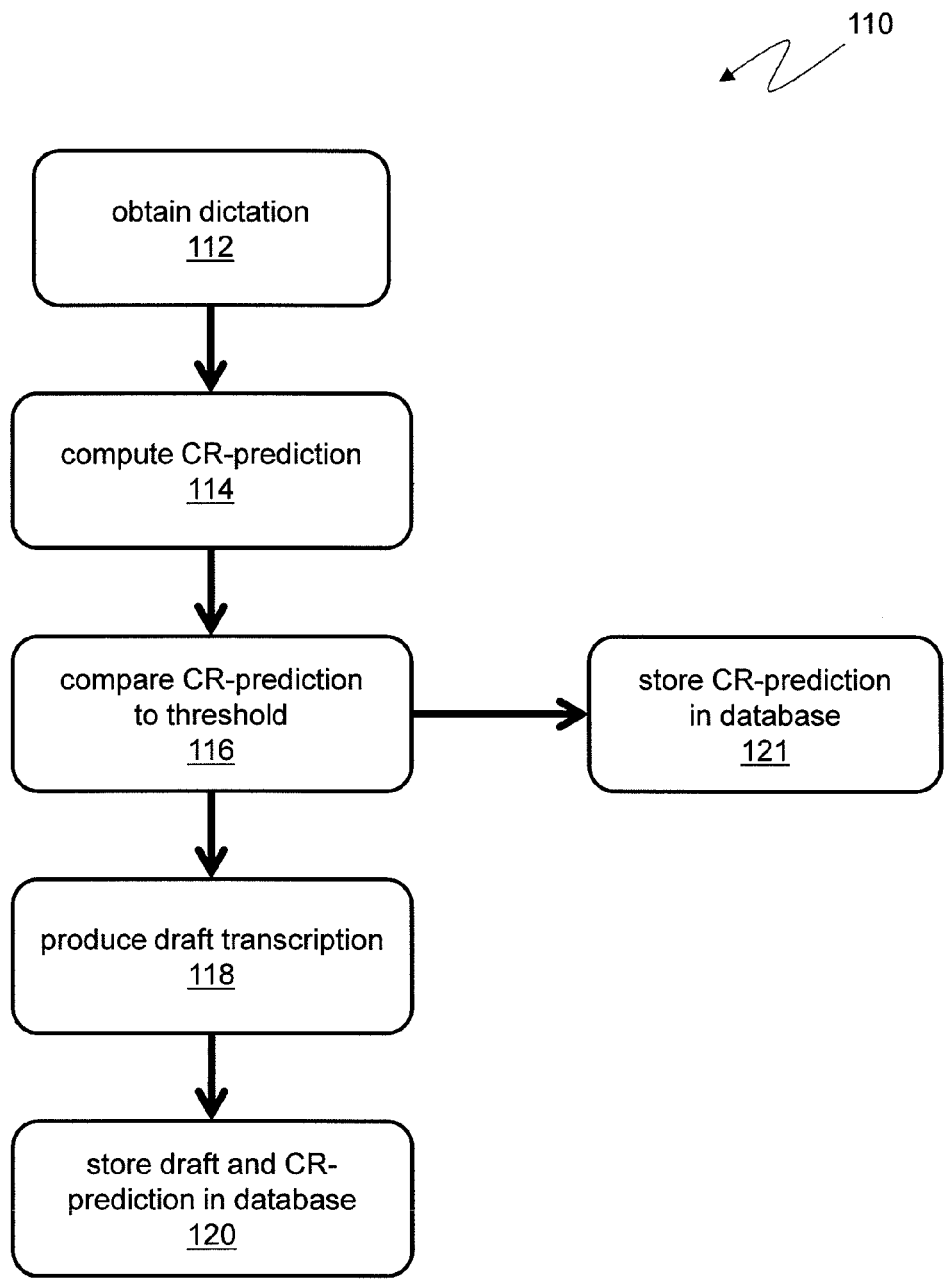
FIG. 5 is a block flow diagram of the automatic speech recognition process.

Referring to FIG. 5, with further reference to FIGS. 1-3, a process 110 of determining a correction rate prediction value using system 10, and in particular the automatic transcription device 30, includes the stages shown. The process 110, however, is exemplary only and not limiting. The process 110 can be altered, e.g., by having stages added, removed, or rearranged.

At stage 112, a dictation is obtained from the database 24. The speaker 12 dictates text that is conveyed through the network 14 to, and stored in, the voice mailbox 18. The dictation is conveyed through the network 22, the database server 24, and the LAN 26 to the automatic transcription device 30. The dictation is associated with a correction rate predictor that is also stored, with the dictation, in the database 24.

At stage 114, a CR-prediction is computed based on the dictation. The ASR module 60, with the local CRP module 64, computes a metric that indicates the quality of a dictation for draft creation. Features of the dictation are combined with a classifier to that is trained to predict the correction rate for the dictation.

At stage 116, the CR-prediction is compared to the threshold to determine whether a draft transcription should be produced for the dictation. For example, if the CR-prediction is lower as compared to the threshold value, a draft transcription is ready for production. At stage 118, a draft is produced and stored in the database in association with the CR-prediction, stage 120. If it is determined that a draft should not be produced based on the CR-prediction, the process of creating a draft transcription is stopped and the CR-prediction is stored in the database, stage 121.

Figure 6:
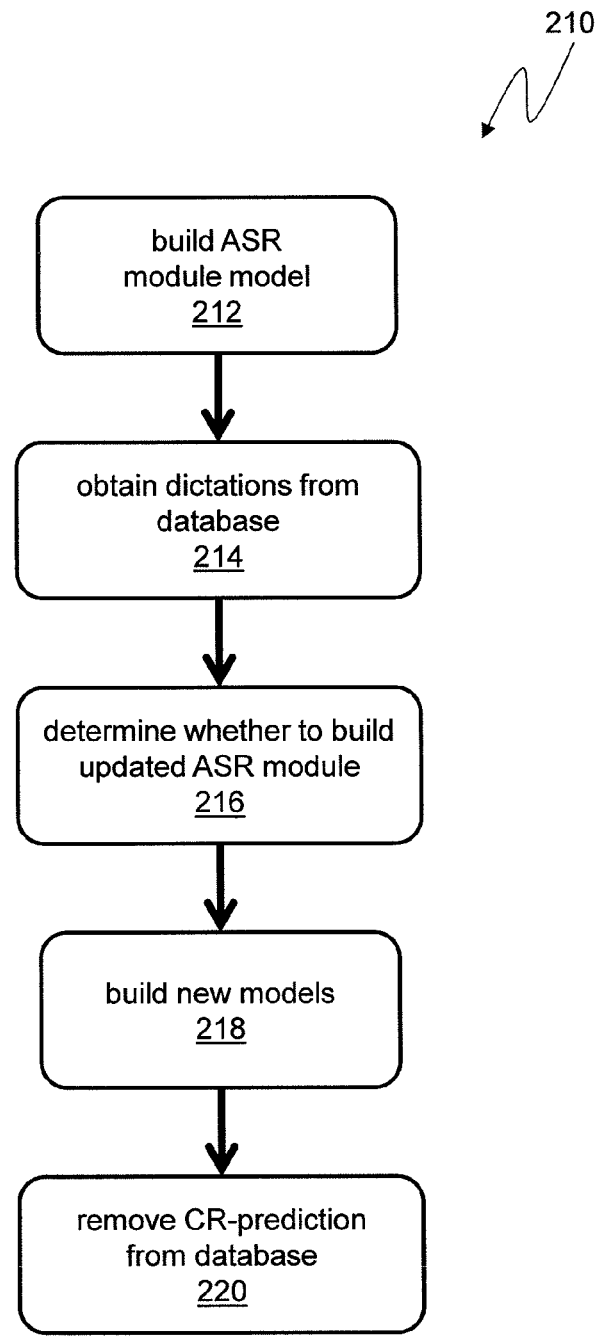
FIG. 6 is a block flow diagram of a process of creating, or removing, a correction rate predictor associated with a speaker or speaker-worktype.

Referring to FIG. 6, with further reference to FIGS. 1-3, a process 210 of creating a correction rate predictor using system 10, and in particular the CRP builder 42, includes the stages shown. The process 210, however, is exemplary only and not limiting. The process 210 can be altered, e.g., by having stages added, removed, or rearranged.

At stage 212, an initial ASR module model is built in the model builder 29. For example, ASR models such as acoustic models, language models, and formatting models are built in the model builder. The models can be built using a small amount of training data, or with no training data (i.e., the models can be speaker-dependent or speaker-independent, for example). Also, at stage 212, a correction rate predictor is built for the speaker to whom the dictation is associated. The CRP builder 28 builds the CR-predictor based on existing draft transcriptions and the associated edited transcriptions completed by a particular speaker. The CRP builder 28 can build the CR-predictor substantially simultaneously with the CR-predictor being built by the ASR module.

At stage 214, dictations associated with a speaker are sent from the database to the automatic transcription device 30. The CR-predictor is also sent to the automatic transcription device 30. The dictations are filtered according to those dictations that are prepared for draft and those that are not in a condition for draft. The dictations are filtered according to the process of FIG. 5.

At stage 216, the system 10 is monitored to detect whether there is sufficient training data to build an updated ASR model for a speaker. For example, the models in the ASR module can be updated when a speaker completed a particular number of dictations in a specified amount of time. At stage 218, the model builder builds new models.

At stage 220, the CR-predictor is removed from the database based on the completion of the new models. Draft transcriptions are created from substantially all of the dictations from a speaker.

Figure 7:
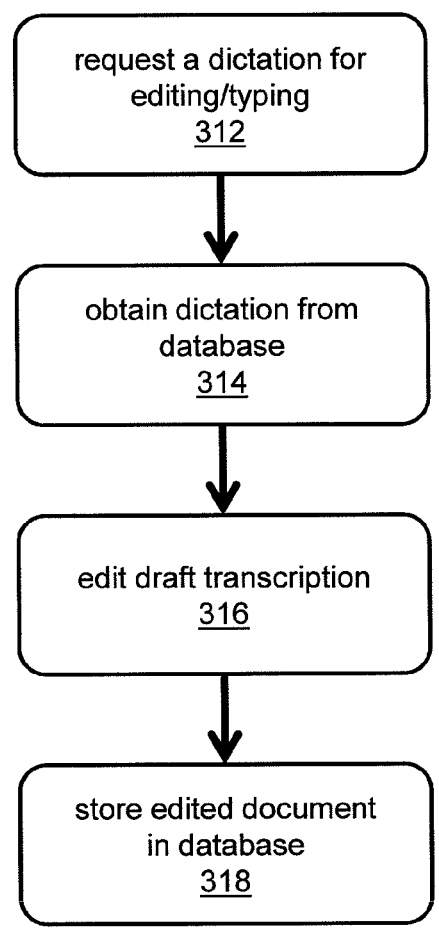
FIG. 7 is a block flow diagram of a process by which dictations are distributed for editing.

Referring to FIG. 7, with further reference to FIGS. 1-3, a process 310 of editing a transcribed document using system 10, and in particular the CRP builder 42, includes the stages shown. The process 310, however, is exemplary only and not limiting. The process 310 can be altered, e.g., by having stages added, removed, or rearranged.

At stage 312, a medical transcriptionist at an editing station requests a dictation for transcription from the database. At this point, a draft transcription has been created for some portion of, or all of a dictation, and a CR-prediction is stored with the draft transcription. The draft is preferably uploaded to the database 40. An indicator is stored with each medical transcriptionist to indicate whether the transcriptionist can edit a transcription, as opposed to typing a document from a dictation. If a medical transcriptionist can edit, a CR-prediction threshold value is stored in the database 40 with the medical transcriptionist's properties. The threshold value is the maximum value of a CR-prediction associated with a draft transcription which a medical transcriptionist is allowed to edit (i.e., the transcriptionist is allowed to edit transcriptions having CR-predictions at or below the threshold value associated with that transcriptionist).

At stage 314, a dictation is obtained for transcription. At stage 315, the CR-prediction associated with a transcription of a dictation is compared to the CR-prediction threshold stored with the medical transcriptionist's properties. For a transcriptionist who has no CR-prediction threshold and there are editing jobs to complete, the transcriptionist receives a high-priority editing job from the database. If the transcriptionist can edit and has a CR-prediction threshold, and there are available editing jobs having a CR-prediction less than or equal to that threshold, the transcriptionist receives a high priority editing job having such a CR designation. If the transcriptionist cannot edit, the transcriptionist receives a typing job based on availability of such jobs.

At stage 316, the draft transcription is edited by the medical transcriptionist. The transcriptionist retrieves the draft transcription stored in the database 40 via the network 22. The transcriptionist edits the draft transcription using the editing device 20. Upon completion of the editing process, at stage 318, the edited document is uploaded to the database 40, and the transcriptionist can choose another document for editing, provided there are draft transcriptions with correction rate predictions within the transcriptionist's personal threshold.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. For example, the CRP builder 28 may be disposed wholly or partially elsewhere (i.e., at the automatic transcription device 30 rather than in a separate CRP builder), such as at the database server 24.

In other embodiments, for example, the CR predictor development can be structured as a decision-tree, such that early branches in the tree are based on features that are inexpensive to compute (e.g. noise level and average spectrum), and later branches are based on more expensive features (e.g. per-word confidence distribution). The CR predictor reveals early in the process that some dictations should be abandoned, while others may require more processing. The CR predictor may function as a means to save computation in the ASR module 60 in the event that a draft is not produced for editing. The ASR output data (word lattices, word alignments, energy values, etc.) can be stored at the time each dictation is recognized and the code that re-computes this data may not exist in the CRP module.

In embodiments of the invention, the correction rate predictor can be trained in many ways. For example, the predictor can be trained based on: data from many speakers at many hospitals for many worktypes; a subset of data by hospital, speaker, worktype or combinations of these; a number of features as input into the classifier, based on prior knowledge of which features are likely to work best in particular circumstances; and statistical techniques to decide which features give desired predictor characteristics.

While the description above focused on medical transcriptions, the invention is not limited to medical transcriptions. The invention may be applied to selecting dictations for non-medical applications such as legal dictations, psychological evaluations, etc. Further, while the discussion above refers to "the invention," more than one invention may be disclosed.

What is claimed is:

1. A non-transitory computer-readable medium encoded with a computer program product for computing a correction rate predictor for medical record dictations, the computer program product comprising computer-readable instructions for causing a computer to:
    initiate automatic speech recognition processing of a dictation to initiate producing a draft medical transcription of at least a portion of the dictation;
    determine features of at least a portion of the dictation to produce a feature set comprising a combination of features of the dictation, the features being relevant to a quantity of expected transcription errors in the transcription of the at least a portion of the dictation;
    analyze the feature set to compute a predicted correction rate associated with the at least a portion of the dictation;
    use the predicted correction rate to determine whether to abandon the automatic speech recognition processing prior to automatic speech recognition processing of all of the dictation;
    use the predicted correction rate to determine whether to provide at least a portion of the draft medical transcription of the at least a portion of the dictation to a transcriptionist; and
    provide the at least a portion of the draft medical transcription to the transcriptionist if the predicted correction rate is below a threshold.

2. The computer-readable medium of claim 1 wherein the instructions further cause a computer to:
    compute an actual correction rate by comparing the draft medical transcription associated with the dictation and a corresponding edited transcription, and counting a number of changes to produce the edited transcription from the draft medical transcription; and
    compute a correction rate prediction error by comparing the predicted correction rate to the actual correction rate.

3. The computer-readable medium of claim 2 wherein the instructions further cause a computer to modify the correction rate predictor to reduce the prediction error between the predicted correction rate and the actual correction rate.

4. The computer-readable medium of claim 2 wherein instructions for causing a computer to obtain a draft medical transcription of a dictation cause the computer to produce a draft transcription only if a predicted correction rate associated with the dictation is below a threshold value.

5. The computer-readable medium of claim 4 wherein instructions further cause the computer to compute the threshold value by analyzing a behavior of the correction rate predictor on a subset of dictations that are stored in the database.

6. The computer-readable medium of claim 1 wherein the features include an element selected from the group consisting of: a background noise measure, signal-to-noise ratio, average spectrum, and overall audio quality measure.

7. The computer-readable medium of claim 1 wherein the instructions for causing the computer to determine features cause the computer to determine features for the entire dictation.

8. The computer-readable medium of claim 1 wherein the instructions for causing the computer to store the predicted correction rate cause the computer to retrieve the correction rate predictor in accordance with at least one of a worktype, a speaker, a speaker-worktype pair, or a specialty associated with the dictation.

9. The computer-readable medium of claim 1, wherein the instructions further cause the computer to use the predicted correction rate to determine whether to provide at least a portion of the draft medical transcription to a transcriptionist by comparing the predicted correction rate to a threshold and determining that the at least a portion of the draft medical transcription is to be provided to a transcriptionist when the predicted correction rate is below the threshold.

10. The computer-readable medium of claim 1, the computer-readable instructions further causing the computer to combine the features into a classifier according to an artificial neural network.

11. The computer-readable medium of claim 3, wherein the computer-readable instructions further cause the computer to weigh more heavily errors from recent transcriptions than from earlier transcriptions.

12. The computer-readable medium of claim 1, wherein the computer-readable instructions further cause the computer to associate a pseudo correction rate with the at least a portion of the dictation for a draft transcript of the at least a portion of the dictation that was not initially edited.

13. The computer-readable medium of claim 1, wherein at least one feature is specific to a selected word in a raw word recognition output.

14. The computer-readable medium of claim 1, wherein the features are structured in a decision tree such that features first analyzed in the tree comprise features that are less computationally expensive to compute than later features in the tree.

15. An automatic transcription system for processing a medical dictation, the system comprising:
    at least one processor programmed to:
        initiate automatic speech recognition processing of a dictation to initiate producing a draft transcription of at least a portion of the dictation;
        compute a correction rate prediction for the at least a portion of the dictation by analyzing a plurality of features of the dictation, the correction rate prediction indicating a quality of the at least a portion of the dictation for production of the draft transcription;

use the correction rate prediction to determine whether to abandon the automatic speech recognition processing prior to automatic speech recognition processing of all of the at least a portion of the dictation; and produce the draft transcription for editing if and only if the correction rate prediction for the at least a portion of the dictation meets a criterion.

16. The automatic transcription system of claim 15, wherein the at least one processor is further programmed to compare the correction rate prediction to a threshold value to determine whether to produce the draft transcription for the dictation.

17. The automatic transcription system of claim 15, wherein the at least one processor is further programmed to produce a draft transcription for a portion of a dictation based on the correction rate prediction for a portion of the dictation.

18. The automatic transcription system of claim 17, wherein the at least one processor is further programmed to store the draft transcription and the correction rate prediction for the dictation in a database.

19. The automatic transcription system of claim 18 wherein the correction rate prediction stored in the database identifies whether a specific user utilizes the draft transcription.

20. The automatic transcription system of claim 15 wherein the plurality of features comprises a background noise measure, signal-to-noise ratio, average spectrum, and/or overall audio quality measure.

21. A method comprising acts of:
(A) initiating automatic speech recognition processing of a medical dictation to initiate producing a draft medical transcription of at least a portion of the dictation;
(B) determining, by at least one processor, features of at least a portion of the medical dictation to produce a feature set comprising a combination of features of the medical dictation, the features being relevant to a quantity of expected transcription errors in the transcription of the at least a portion of the medical dictation;
(C) analyzing, by the at least one processor, at least part of the feature set to compute a predicted correction rate associated with the at least a portion of the medical dictation;
(D) comparing, by the at least one processor, the predicted correction rate to a threshold;
(E) abandoning the automatic speech recognition processing prior to automatic speech recognition processing of all of the medical dictation when the predicted correction rate meets or exceeds the threshold;
(F) providing, by the at least one processor, at least a portion of the draft medical transcription to a transcriptionist when the predicted correction rate is below the threshold; and
(G) refraining, by the at least one processor, from providing the at least a portion of the draft medical transcription to the transcriptionist for editing when the predicted correction rate meets or exceeds the threshold.

22. The method of claim 21, further comprising an act of:
(H) instructing the transcriptionist to transcribe the at least a portion of the medical dictation without editing the draft medical transcription when the predicted correction rate is at or above the threshold.

23. The method of claim 21 wherein the features include an element selected from the group consisting of: a background noise measure, signal-to-noise ratio, average spectrum, and overall audio quality measure.

24. The method of claim 21, wherein the act (A) further comprises obtaining the draft medical transcription from an automatic speech recognition system.

* * * * *